United States Patent [19]

Glock et al.

[11] Patent Number: 5,556,828
[45] Date of Patent: Sep. 17, 1996

[54] SAFENED DIMETHENAMID HERBICIDAL COMPOSITIONS

[75] Inventors: Jutta Glock, Mumpf, Switzerland; Elmar Kerber, Görwihl, Germany

[73] Assignee: Ciba-Geigy Corporation, Tarrytown, N.Y.

[21] Appl. No.: 348,508

[22] Filed: Dec. 1, 1994

Related U.S. Application Data

[63] Continuation of Ser. No. 214,738, Mar. 17, 1994, abandoned.

[30] Foreign Application Priority Data

Mar. 22, 1993 [CH] Switzerland ............... 855/93
Apr. 15, 1993 [CH] Switzerland ............. 1145/93

[51] Int. Cl.$^6$ .................................. A01N 25/32
[52] U.S. Cl. ............... 504/105; 504/106; 504/107; 504/108; 504/112
[58] Field of Search .................. 504/108, 105, 504/106, 107, 112

[56] References Cited

U.S. PATENT DOCUMENTS

| | | | |
|---|---|---|---|
| 3,959,304 | 5/1976 | Teach | 71/90 |
| 4,256,481 | 3/1981 | Gardi et al. | 71/88 |
| 4,392,882 | 7/1983 | Riebel et al. | 71/92 |
| 4,448,960 | 5/1984 | Rohr et al. | 544/282 |
| 4,579,691 | 4/1986 | Maier et al. | 558/159 |
| 4,601,745 | 7/1986 | Moser | 71/88 |
| 4,666,502 | 5/1987 | Seckinger et al. | 71/90 |
| 4,708,735 | 11/1987 | Pallos et al. | 71/118 |
| 4,734,119 | 3/1988 | Diel et al. | 71/86 |
| 4,739,093 | 4/1988 | Diel et al. | 558/154 |
| 4,846,880 | 7/1989 | Alt et al. | 71/94 |
| 4,897,109 | 1/1990 | Martin | 71/118 |
| 4,971,618 | 11/1990 | Pallos et al. | 71/93 |
| 5,028,256 | 7/1991 | Martin | 71/118 |
| 5,116,402 | 5/1992 | Dutka et al. | 71/88 |

FOREIGN PATENT DOCUMENTS

| | | |
|---|---|---|
| 0023305 | 2/1981 | European Pat. Off. . |
| 0031686 | 7/1981 | European Pat. Off. . |
| 0054278 | 6/1982 | European Pat. Off. . |
| 0126710 | 11/1984 | European Pat. Off. . |
| 0143078 | 5/1985 | European Pat. Off. . |
| 0149974 | 7/1985 | European Pat. Off. . |
| 0163607 | 12/1985 | European Pat. Off. . |
| 0304409 | 2/1989 | European Pat. Off. . |
| 0531271 | 10/1993 | European Pat. Off. . |
| 2948535 | 6/1981 | Germany . |
| 3303388 | 8/1983 | Germany . |

OTHER PUBLICATIONS

Bussler. CA 119(7):65659s. Abstract of EP 531271. Mar. 10, 1993.
Miller et al. CA 117 (5): 42741g. Abstract of EP 480902. Apr. 15, 1992.
Viger et al. CA 115 (25): 273381q. *Weed Sci*: 39 (3): 324–8. 1991.

*Primary Examiner*—S. Mark Clardy
*Attorney, Agent, or Firm*—George Dohmann; Marla J. Mathias; William A. Teoli, Jr.

[57] ABSTRACT

Mixtures of a herbicidally effective amount of a haloacetamide of formula I

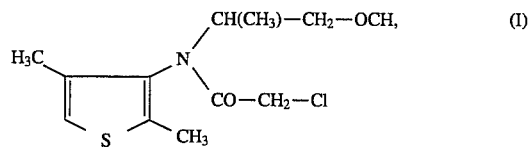

and, to antagonize the herbicide, an antidotally effective amount of a compound of formula II

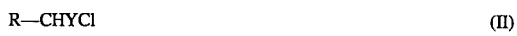

wherein R is defined herein, suitable for controlling weeds in crops of cultivated plants, particularly maize.

16 Claims, No Drawings

SAFENED DIMETHENAMID HERBICIDAL COMPOSITIONS

This is a continuation of Ser. No. 08/214,738, filed Mar. 17, 1994, abandoned.

The present invention relates to a selective herbicidal composition for controlling grasses and weeds in crops of cultivated plants, especially in crops of maize, which composition comprises a herbicide and a safener (antidote) and protects the cultivated plants, but not the weeds, from the phytotoxic action of the herbicide, and to the use of said composition or combination of herbicide and safener for controlling weeds in crops of cultivated plants.

When applying herbicides, the cultivated plants may also suffer severe damage owing to factors that include the concentration of the herbicide and the mode of application, the cultivated plant itself, the nature of the soil, and the climatic conditions such as exposure to light, temperature and rainfall.

To counteract this problem and similar ones, the proposal has already been made to use different compounds as safeners which are able to antagonise the harmful action of the herbicide on the cultivated plant, i.e. to protect the cultivated plant while leaving the herbicidal action on the weeds to be controlled virtually unimpaired. It has, however, been found that the proposed safeners often have a very specific action, not only with respect to the cultivated plants but also to the herbicide, and in some cases also subject to the mode of application, i.e. a specific safener will often be suitable only for a specific cultivated plant and a specific class of herbicide.

It has now been found that certain chloroacetamides are suitable for protecting cultivated plants from the phytotoxic action of the compound of formula I

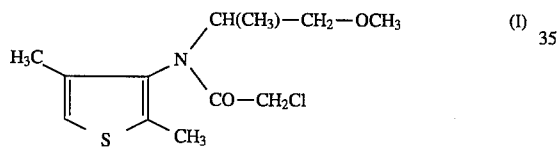

Accordingly, the invention provides a selective herbicidal composition comprising, in addition to customary inert formulation assistants such as carders, solvents and wetting agents, a mixture of a) a herbicidally effective amount of a compound of formula I

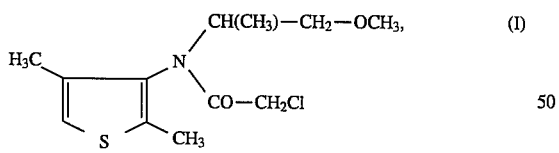

and b) to antagonise the herbicide, an antidotally effective amount of a compound of formula I R—CHYCl    (II)

wherein R is a radical of formula

wherein $R_{33}$ and $R_{34}$ are each independently of the other $C_1$–$C_6$alkyl or $C_2$–$C_6$alkenyl; or $R_{33}$ and $R_{34}$, taken together, are

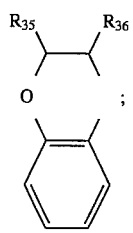

$R_{35}$ and $R_{36}$ are each independently of the other hydrogen or $C_1$–$C_6$alkyl; or $R_{33}$ and $R_{34}$, taken together are

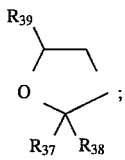

$R_{37}$ and $R_{38}$ are each independently of the other $C_1$–$C_4$alkyl, or $R_{37}$ and $R_{38}$, taken together, are —$(CH_2)_5$—;

$R_{39}$ is hydrogen, $C_1$–$C_4$alkyl or

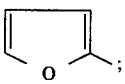

or $R_{33}$ and $R_{34}$, taken together, are

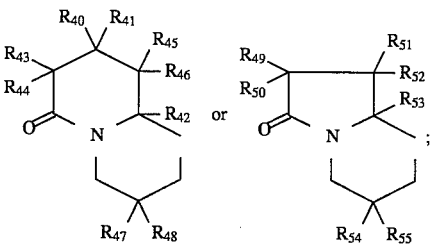

$R_{40}$, $R_{41}$, $R_{42}$, $R_{43}$, $R_{44}$, $R_{45}$, $R_{46}$, $R_{47}$, $R_{48}$, $R_{49}$, $R_{50}$, $R_{51}$, $R_{52}$, $R_{53}$, $R_{54}$ and $R_{55}$ are each independently of one another hydrogen or $C_1$–$C_4$alkyl, or R is a radical of formula

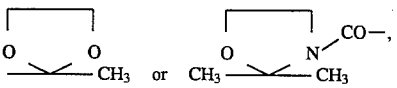

or R is a radical of formula

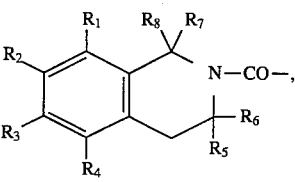

wherein $R_1$, $R_2$, $R_3$ and $R_4$ are each independently of one another hydrogen, $C_1$–$C_4$alkyl, $C_1$–$C_4$alkoxy or $C_1$–$C_4$haloalkyl, $R_5$, $R_6$, $R_7$ and $R_8$ are each independently of one another hydrogen, $C_1$–$C_4$alkyl or $C_1$–$C_4$haloalkyl, or R is a radical of formula

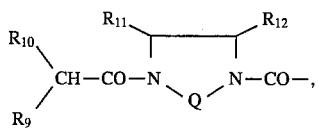

wherein $R_9$ is $C_1$–$C_4$alkyl or halogen, $R_{10}$ is halogen, $R_{11}$ and $R_{12}$ are each independently of the other hydrogen or $C_1$–$C_4$alkyl, and Q is $C_1$–$C_4$alkylene or alkyl-substituted $C_1$–$C_4$alkylene, or R is a radical of formula

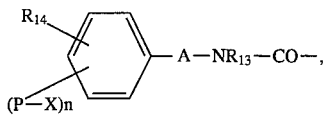

wherein $R_{14}$ is hydrogen, halogen, $C_1$–$C_4$alkyl, dioxymethylene, $C_1$–$C_4$alkoxy, $C_2$–$C_4$alkenyloxy, $C_2$–$C_4$alkynyloxy or cyano-$C_1$–$C_4$alkyl, P is $C_1$–$C_4$alkyl, $C_2$–$C_4$ alkenyl, $C_2$–$C_4$alkynyl, $C_3$–$C_8$cycloalkyl, $C_1$–$C_4$alkoxy-$C_1$–$C_4$alkyl, $C_2$–$C_4$ alkeneoxy-$C_1$–$C_{46}$alkyl, $C_2$–$C_4$alkyneoxy-$C_1$–$C_4$alkyl, $C_1$–$C_4$alkylthio-$C_1$–$C_4$ alkyl, $C_2$–$C_4$alkenylthio-$C_1$–$C_4$alkyl, $C_2$–$C_4$alkynylthio-$C_1$–$C_4$alkyl, $C_1$–$C_4$alkylsulfinyl-$C_1$–$C_4$alkyl, $C_1$–$C_4$alkylsulfonyl-$C_1$–$C_4$alkyl, halo-$C_1$–$C_4$alkyl, cyano-$C_1$–$C_4$alkyl, 2,2-di-$C_1$–$C_4$alkoxy-$C_1$–$C_4$alkyl, 1,3-dioxolan-2-yl-$C_1$–$C_4$alkyl, 1,3-dioxolan-4-yl-$C_1$–$C_4$alkyl,2,2-di-$C_1$–$C_4$alkyl-1,3-dioxolan-4-yl-$C_1$ –$C_4$alkyl, 1,3-dioxan-2-yl-$C_1$–$C_4$alkyl,2-benzopyranyl-$C_1$–$C_4$alkyl, $C_1$–$C_4$ alkoxycarbonyl or $C_2$–$C_4$alkenyloxycarbonyl or tetrahydrofurfuryl-$C_1$–$C_4$alkyl; the group P-X may also be halogen-$C_1$–$C_4$alkyl, X, O, S, SO or $SO_2$, n, 1, 2 or 3, A is a $C_1$–$C_8$hydrocarbon radical or $C_1$–$C_8$hydrocarbon radical which is substituted by alkoxy, alkylthio, fluoro, cyano or haloalkyl, and $R_{13}$ is hydrogen, a $C_1$–$C_5$hydrocarbon radical, a $C_1$–$C_5$hydrocarbon radical which is substituted by alkoxy, polyalkoxy, halogen, cyano or trifluoromethyl, $C_3$–$C_8$cycloalkyl, $C_1$–$C_4$alkyl-$C_3$–$C_8$cycloalkyl, di-$C_1$–$C_4$ alkoxy-$C_1$–$C_4$alkyl, 1,3-dioxolan-2-yl-$C_1$–$C_4$alkyl, 1,3-dioxolan-4-yl-$C_1$–$C_4$alkyl, 1,3-dioxan-2 -yl-$C_1$–$C_4$alkyl, furyl-$C_1$–$C_4$alkyl, tetrahydrofuryl-$C_1$–$C_4$alkyl or a radical of formula —$NHCO_2R_{01}$, —$CH_2CO_2R_{01}$,—$CH(CH_3)CO_2R_{01}$ or —$CH(R_{02})$—$C(R_{03})$=$NOR_{04}$, wherein $R_{01}$ is methyl, ethyl, propyl, isopropyl or allyl, $R_{02}$ and $R_{03}$ are each hydrogen or $C_1$–$C_4$alkyl, and $R_{04}$ is hydrogen, $C_1$–$C_4$alkyl, $C_2$–$C_4$alkenyl or $C_2$–$C_4$ alkynyl, or R is a radical of formula $(H_5C_2O)_2P(O)CH_2NHCO$— or

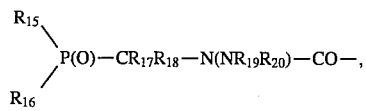

wherein $R_{15}$ and $R_{16}$ are each independently of the other hydroxyl, $C_1$–$C_4$alkyl, aryl, $C_1$–$C_4$alkoxy, $C_2$–$C_4$alkenyloxy, $C_2$–$C_4$ alkynyloxy, $C_2$–$C_4$haloalkoxy, $C_2$–$C_8$alkoxyalkoxy, $C_1$–$C_4$cyanoalkoxy, $C_1$–$C_4$ phenylalkoxy or aryloxy, or aryloxy which is substituted by halogen, cyano, nitro or $C_1$–$C_4$alkoxy, $R_{17}$ is hydrogen, $C_1$–$C_4$alkyl or phenyl, or phenyl which is substituted by halogen, cyano, nitro or $C_1$–$C_4$alkoxy, $R_{18}$ is hydrogen, or $C_1$–$C_4$alkyl, $R_{19}$ is hydrogen or a radical of formula —$COCX_1X_2$-$R_{06}$ or a halogen-substituted alkenoyl radical containing 2 to 4 carbon atoms in the alkenyl moiety, wherein $X_1$ and $X_2$ are each independently of the other halogen, or a radical of formula —$COOR_{07}$ or —$COR_{08}$ or a $C_1$–$C_4$alkyl, $C_1$–$C_4$alkenyl or $C_1$–$C_4$phenylalkyl radical which can be substituted at the phenyl ring by halogen, cyano, nitro or $C_1$–$C_4$alkoxy, and $R_{20}$ is hydrogen, $C_1$–$C_4$alkyl, $C_2$–$C_4$ alkenyl or $C_2$–$C_4$alkynyl, $R_{06}$ is hydrogen, halogen or $C_1$–$C_6$alkyl, $R_{07}$ is $C_1$–$C_4$alkyl, $C_1$–$C_4$phenylalkyl or $C_1$–$C_4$phenylalkyl which is substituted in the phenyl nucleus by halogen, cyano, nitro or $C_1$–$C_4$alkoxy, and $R_{08}$ is $C_1$–$C_4$alkyl, $C_2$–$C_4$alkenyl, $C_2$–$C_4$ alkynyl, phenyl, $C_1$–$C_4$phenylalkyl or $C_1$–$C_4$phenylalkyl which is substituted in the phenyl nucleus by halogen, cyano, nitro or $C_1$–$C_4$alkoxy, or R is a radical of formula

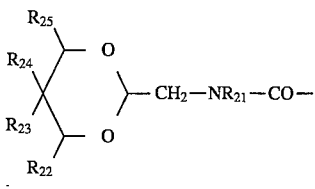

or of formula

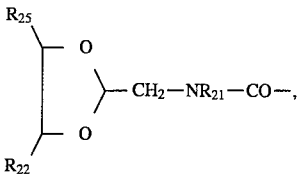

wherein $R_{21}$ is methyl, ethyl, propyl, 1-methylethyl, 2-propenyl, 2-butenyl, 1,1-dimethyl-2-propenyl, 2-propynyl or 2-methyl-2-propynyl, and $R_{22}$, $R_{23}$, $R_{24}$ and $R_{25}$ are each independently of one another hydrogen or methyl, and Y is chloro, or Y is hydrogen if R is a radical of formula $(H_5C_2O)_2P(O)CH_2NHCO$—.

The alkyl radicals referred to in connection with the compounds of formulae I and II may be straight-chain or branched and are typically methyl, ethyl, propyl, butyl, pentyl and hexyl, as well as branched isomers thereof. Suitable alkenyl radicals are derived from the cited alkyl radicals. Aryloxy is preferably phenoxy and naphthoxy. By hydrocarbon radicals are meant monovalent or divalent saturated or unsaturated straight-chain or branched or saturated or unsaturated cyclic radicals of carbon and hydrogen, typically alkyl, cycloalkyl, alkenyl, alkynyl, cycloalkenyl and phenyl.

The invention further relates to the use of the novel composition for controlling weeds and grasses in crops of cultivated plants, especially maize.

Compounds of formula II preferably used in the novel composition are those wherein R is a radical of formula

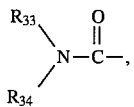

wherein $R_{33}$ and $R_{34}$ together are

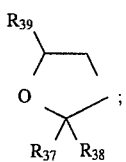

$R_{37}$ and $R_{38}$ are each independently of the other $C_1$–$C_4$alkyl; or $R_{37}$ and $R_{38}$ together are —$(CH_2)_5$-; and $R_{39}$ is hydrogen, $C_1$–$C_4$alkyl or

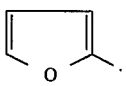

Illustrative examples of especially suitable compounds of formula II are listed in the following Tables 1 and 2.

TABLE 1

Compounds of formula II $$R_{33}\diagdown \underset{R_{34}}{N}-\underset{\|}{\overset{O}{C}}-CHCl_2 \qquad (II)$$

| Cmpd. No. | $R_{33}$ | $R_{34}$ | $R_{33} + R_{34}$ |
|---|---|---|---|
| 1.001 | $CH_2$=$CHCH_2$ | $CH_2$=$CHCH_2$ | — |
| 1.002 | — | — | $-O-C(CH_3)_2-$ (dimethyl dioxy ring fragment) |
| 1.003 | — | — | $CH_3$-substituted dimethyl dioxy ring fragment |
| 1.004 | — | — | 1-oxa-spiro[cyclohexane] fragment |
| 1.005 | — | — | furan-2-yl substituted dimethyl dioxy fragment |
| 1.006 | — | — | 2-methylphenyl-CH(CH_3)CH_2- fragment |
| 1.007 | — | — | 2,2,6-trimethyl-piperidinyl-carbonyl fragment |
| 1.008 | — | — | 1,5-dioxa-spiro[5.5]undecane fragment |

TABLE 1-continued

Compounds of formula II $$R_{33}\diagdown N-\overset{O}{\overset{\|}{C}}-CHCl_2 \atop R_{34}\diagup \qquad (II)$$

| Cmpd. No. | $R_{33}$ | $R_{34}$ | $R_{33} + R_{34}$ |
|---|---|---|---|
| 1.009 | — | — | 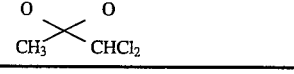 |
| 1.010 | 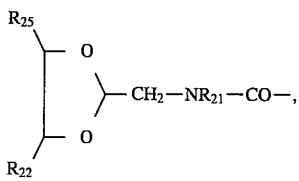 | $CH_2=CHCH_2$ | — |
| 1.011 | 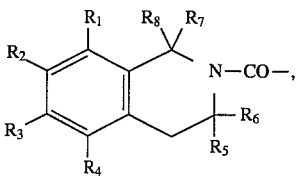 | $(CH_3)_2CH-$ | — |

TABLE 2

Compounds of formula II

| 2.1 | $(C_2H_5O)_2P(O)-CH_2-NHCO-CH_2-Cl$ |
|---|---|
| 2.2 | 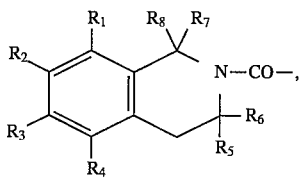 |

Another group of preferred compounds of formula II, wherein R is a radical of formula

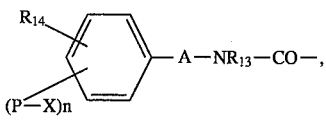

wherein $R_{21}$ is methyl, ethyl, propyl, 2-propenyl or 2-butenyl, $R_{22}$ and $R_{25}$ are hydrogen. Among these compounds, the compound in which $R_{21}$ is 2-propenyl is preferred.

Those compounds of formula II are also preferred in which R is a radical of formula

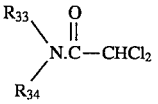

wherein $R_1$ to $R_8$ are each independently of one another hydrogen or $C_1$–$C_4$alkyl. Those compounds are particularly suitable in which $R_1$ to $R_7$ are hydrogen and $R_8$ is methyl.

In another group of particularly suitable compounds R is a radical of formula

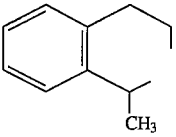

wherein $R_1$ to $R_8$ are each independently of one another hydrogen or $C_1$–$C_4$alkyl. Those compounds in which $R_1$ to $R_7$ are hydrogen and $R_8$ is methyl are particularly suitable.

In another group of particularly suitable compounds, R is a radical of formula

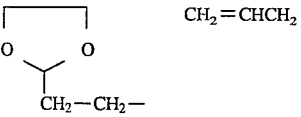

wherein $R_{14}$ is hydrogen, $C_1$–$C_4$alkyl or $C_1$–$C_4$alkoxy, P is $C_1$–$C_4$alkyl, $C_2$–$C_4$alkenyl or $C_2$–$C_4$ alkynyl, X is O or S, n is 1, A is a $C_1$–$C_8$hydrocarbon radical and $R_{13}$ is hydrogen or a $C_1$–$C_5$hydrocarbon radical. Among this group of compounds, those compounds of formula II are preferred in which $R_{14}$ is $C_1$–$C_4$alkoxy, P is $C_1$–$C_4$alkyl, X is O, A is $C_1$–$C_4$alkylene and $R_{13}$ is $C_1$ –$C_4$alkyl. The compound in which $R_{14}$ is methoxy, P is methyl, A is methylene and $R_{13}$ is isopropyl, is of particular interest.

A further group of preferred compounds of formula II embraces those compounds wherein R is a radical of formula

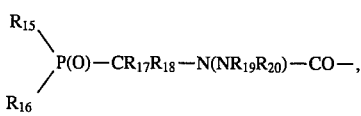

wherein $R_{15}$ and $R_{16}$ are each independently of the other hydroxyl, $C_1$–$C_4$alkyl or $C_1$–$C_4$alkoxy, $R_{17}$ and $R_{18}$ are each independently of the other hydrogen or $C_1$–$C_4$alkyl, and $R_{19}$ is hydrogen or a radical of formula —COOR$_{07}$, wherein $R_{07}$ is $C_1$–$C_4$alkyl, and $R_{20}$ is hydrogen or $C_1$–$C_4$alkyl. Preferably $R_{16}$ and $R_{15}$ are $C_1$–$C_4$alkoxy, $R_{17}$ and $R_{18}$ are hydrogen, $R_{19}$ is a radical of formula —COOR$_{07}$, wherein $R_{07}$ is $C_1$–$C_4$alkyl, and $R_{20}$ is hydrogen. The compound in which $R_{15}$ and $R_{16}$ are isopropoxy and $R_{19}$ is —COOC$_2$H$_5$ is of particular importance.

Especially suitable compositions comprise as compound of formula II a compound of formula III

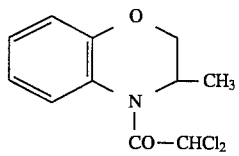 (III)

or of formula IV

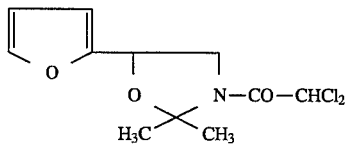 (IV)

or of formula V

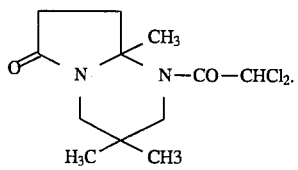 (V)

The compound of formula I used in the practice of this invention and the preparation thereof are disclosed, inter alia, in DE-A-3 303 388. The compounds of formula II used for the novel compositions and and their preparation are disclosed, inter alia, in U.S. Pat. No. 4,971,618, U.S. Pat. No. 3,959,304, U.S. Pat. No. 4,256,481, U.S. Pat. No. 4,708,735, EP-A-149 974, EP-A-304 409, EP-A-31 686, EP-A-54 278, EP-A-23 305, U.S. Pat. No. 4,846,880, EP-A-143 078, EP-A-163 607, EP-A-126 710 as well as DE-A-2 948 535.

The invention also relates to a method of selectively controlling weeds in crops of cultivated plants, which comprises treating said cultivated plants, the seeds or seedlings or the crop area thereof, concurrently or separately, with a herbicidally effective amount of the herbicide of formula I and, to antagonise the herbicide, an antidotally effective amount of a compound of formula II.

Suitable cultivated plants which can be protected by the compound of formula II against the harmful action of the aforementioned herbicides are preferably those which are important in the food or textile sector, typically sugar cane and, in particular, millet and maize, as well as flee and other types of cereals such as wheat, rye, barley and oats.

The weeds to be controlled can be monocot as well as dicot weeds.

Crop areas will be understood as meaning the areas already under cultivation with the cultivated plants or seeds thereof, as well as the areas intended for cropping with said cultivated plants.

Depending on the end use, a safener of formula II can be used for pretreating seeds of the crop plants (dressing of seeds of seedlings) or it can be incorporated in the soil before or after sowing. It can, however, also be applied postemergence by itself alone or together with the herbicide. Treatment of the plant or the seeds with the safener can therefore in principle be carded out irrespective of the time of application of the herbicide. Treatment can, however, also be carried out by simultaneous application of the herbicide and safener (e.g. as tank mixture).

The concentration of safener with respect to the herbicide will depend substantially on the mode of application. Where a field treatment is carded out either by using a tank mixture with a combination of safener and herbicide or by separate application of safener and herbicide, the ratio of safener to herbicide will usually be from 1:100 to 1:1, preferably from 1:20 to 1:1 and, most preferably, 1:1, In field treatment it is usual to apply 0.00 1 to 5.0 kg/ha, preferably 0.001 to 0.5 kg/ha, of safener.

The concentration of herbicide is usually in the range from 0.001 to 2 kg/ha, but will preferably be from 0.005 to 1 kg/ha.

The compositions of this invention are suitable for all methods of application commonly used in agriculture, including preemergence application, postemergence application and seed dressing.

For seed dressing, 0.001 to 10 g of safener/kg of seeds, preferably 0.05 to 2 g of safener/kg of seeds, is usually applied. If the safener is used in liquid form shortly before sowing to effect soaking, then it is preferred to use safener solutions that contain the active ingredient in a concentration of 1 to 10,000 ppm, preferably of 100 to 1000 ppm.

For application, it is preferred to process the compound of formula II, or mixture of the compound of formula II and the herbicide of formula I, conveniently together with the assistants conventionally employed in formulation technology to emulsifiable concentrates, coatable pastes, directly sprayable or dilutable solutions, dilute emulsions, wettable powders, soluble powders, dusts, granulates or microcapsules.

The formulations are prepared in known manner, conveniently by homogeneously mixing or grinding, or mixing and grinding, the active ingredients with liquid or solid formulation assistants, typically solvents or solid carders. Surface-active compounds (surfactants) may additionally be used for preparing the formulations.

Suitable solvents may typically be: aromatic hydrocarbons, preferably the fractions containing 8 to 12 carbon atoms such as xylene mixtures or substituted naphthalenes; phthalates such as dibutyl or dioctyl phthalate; aliphatic hydrocarbons such as cyclohexane or paraffins; alcohols and glycols and their ethers and esters such as ethanol, diethylene glycol, 2-methoxyethanol or 2-ethoxyethanol; ketones such as cyclohexanone; strongly polar solvents such as N-methyl-2-pyrrolidone, dimethyl sulfoxide or dimethyl formamide; as well as vegetable oils or epoxidised vegetable oils such as epoxidised coconut oil or soybean oil; or water.

The solid carders typically used for dusts and dispersible powders are usually natural mineral fillers such as calcite, talcum, kaolin, montmorillonite or attapulgite. To improve the physical properties it is also possible to add highly dispersed silicic acid or highly dispersed absorbent polymers. Suitable granulated adsorptive carriers are porous types, including pumice, broken brick, sepiolite or bentonite; and suitable nonsorbent carders are materials such as calcite or sand. In addition, innumerable pregranulated materials of inorganic or organic origin may be used, especially dolomite or pulverised plant residues.

Depending on the safener, and usually also on the herbicide, suitable surface-active compounds are nonionic, cationic and/or anionic surfactants having good emulsifying, dispersing and wetting properties. Surfactants will also be understood as comprising mixtures of surfactants.

Suitable anionic surfactants may be water-soluble soaps as well as water-soluble synthetic surface-active compounds.

Suitable soaps are the alkali metal salts, alkaline earth metal salts, ammonium salts or substituted ammonium salts of higher fatty acids ($C_{10}$–$C_{22}$), e.g. the sodium or potassium salts of oleic or stearic acid, or of natural fatty acid mixtures which can be obtained, inter alia, from coconut oil or tallow oil. Further suitable soaps are also the fatty acid methyl taurin salts.

More often, however, so-called synthetic surfactants are used, especially fatty sulfonates, fatty sulfates, sulfonated benzimidazole derivatives or alkylarylsulfonates.

The fatty alcohol sulfonates or sulfates are usually in the form of alkali metal salts, alkaline earth metal salts, ammonium salts or substituted ammonium salts, and they contain a $C_8$–$C_{22}$alkyl radical which also includes the alkyl moiety of acyl radicals, e.g. the sodium or calcium salt of ligninsulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain two sulfonic acid groups and one fatty acid radical containing 8 to 22 carbon atoms. Illustrative examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Corresponding phosphates, typically salts of the phosphoric acid ester of an adduct of p-nonylphenol with 4 to 14 mol of ethylene oxide, or phospholipids, are also suitable.

Nonionic surfactants are preferably polyglycol ether derivatives of aliphatic or cycloaliphatic alcohols or of saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable nonionic surfactants are the water-soluble polyadducts of polyethylene oxide with polypropylene glycol, ethylenediaminopolypropylene glycol and alkylpolypropylene glycol containing 1 to 10 carbon atoms in the alkyl chain, which polyadducts contain 20 to 250 ethylene glycol ether groups and 10 to 100 propylene glycol ether groups. These compounds usually contain 1 to 5 ethylene glycol units per propylene glycol unit.

Illustrative examples of nonionic surfactants are nonylphenol polyethoxylates, polyethoxylated castor oil, polyadducts of polypropylene and polyethylene oxide, tributylphenol polyethoxylate, polyethylene glycol and octylphenol polyethoxylate, Fatty acid esters of polyoxyethylene sorbitan are also suitable nonionic surfactants, typically polyoxyethylene sorbitan trioleate.

Cationic surfactants are preferably quaternary ammonium salts carrying, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, for example stearyl trimethylammonium chloride or benzyl bis(2-chloroethyl)ethylammonium bromide.

The surfactants customarily employed in the art of formulation are described, inter alia, in "Mc Cutcheon's Detergents and Emulsifiers Annual", Mc Publishing Corp., Glen Rock, N.J., 1988, H. Stache, "Tensid-Taschenbuch" (Handbook of Surfactants), Carl Hanser Verlag, Munich/Vienna 1981, and M. and J. Ash, "Encyclopedia of Surfactants", Vol I–III, Chemical Publishing Co., New York, 1980–81.

The agrochemical compositions will usually contain from 0.1 to 99% by weight, preferably from 0.1 to 95% by weight, of compound of formula II or mixture of safener and herbicide, from 1 to 99.9% by weight, preferably from 5 to 99.8% by weight, of a solid or liquid formulation assistant, and from 0 to 25% by weight, preferably from 0.1 to 25% by weight, of a surfactant.

Whereas it is preferred to formulate commercial products as concentrates, the end user will normally use dilute formulations.

The compositions may also contain further ingredients such as stabilisers, antifoams, viscosity regulators, binders, tackifiers, as well as fertilisers or other chemical agents for achieving special effects.

Different methods and techniques may suitably be used for applying the compounds of formula II or compositions containing them for protecting cultivated plants from the harmful effects of herbicides of formula I, conveniently the following:

i) Seed dressing a) Dressing the seeds with a wettable powder formulation of the compound of formula II by shaking in a vessel until the safener is uniformly distributed on the surface of the seeds (dry treatment), using up to c. 1 to 500 g of compound of formula II (4 g to 2 g of wettable powder) per 100 kg of seeds.

b) Dressing seeds with an emulsifiable concentrate of the compound of formula II by method a) (wet treatment).

c) Dressing by immersing the seeds in a mixture containing 100–1000 ppm of compound of formula II for 1 to 72 hours, leaving them wet or subsequently drying them (seed soaking).

Seed dressing or treatment of the germinated seedlings are naturally the preferred methods of application, as the safener treatment is fully concentrated on the target crop. Usually 1 to 1000 g, preferably 5 to 250 g, of safener is used per 100 kg of seeds. However, depending on the method employed, which also permits the use of other chemical agents or micronutrients, plus or minus deviations from the indicated limiting concentrations are possible (repeat dressing).

ii) Application as a tank mixture

A liquid formulation of a mixture of safener and herbicide (reciprocal ratio from 10:1 to 1:100) is used, the concentration of herbicide being from 0.005 to 5.0 kg/ha. This tank mixture is applied before or after sowing.

iii) Application in the furrow

The safener formulated as emulsifiable concentrate, wettable powder or granulate is applied to the open furrow in which the seeds have been sown. After covering the furrow, the herbicide is applied pre-emergence in conventional manner.

iv) Controlled release of safener

A solution of the compound of formula II is applied to mineral granulate substrates or polymerised granulates (urea/formaldehyde) and allowed to dry. A coating may additionally be applied (coated granulates) which permits controlled release of the safener over a specific period of time.

The invention is illustrated in more detail by the following non-limitative Examples.

Formulation Examples for mixtures of herbicides of formula I and safeners of formula II (throughout, percentages are by weight)

| F1. Emulsifiable concentrates | a) | b) | c) | d) |
|---|---|---|---|---|
| compound mixture | 5% | 10% | 25% | 50% |
| calcium dodecylbenzenesulfonate | 6% | 8% | 6% | 8% |
| polyethoxylated castor oil (36 mol EO) | 4% | — | 4% | 4% |
| octylphenol polyethoxylate (7–8 mol EO) | — | 4% | — | 2% |
| cyclohexanone | — | — | 10% | 20% |
| mixture of aromatic hydrocarbons $C_9$–$C_{12}$ | 85% | 78% | 55% | 16% |

Emulsions of any desired concentration can be prepared by diluting such concentrates with water.

| F2. Solutions | a) | b) | c) | d) |
|---|---|---|---|---|
| compound mixture | 5 | 10% | 50% | 90% |
| 1-methoxy-3-(3-methoxypropoxy)-propane | — | 20% | 20% | — |
| polyethylene glycol 400 | 20% | 10% | — | — |
| N-methyl-2-pyrrolidone | — | — | 30% | 10% |
| mixture of aromatic hydrocarbons $C_9$–$C_{12}$ | 75% | 60% | — | — |

The solutions are suitable for use as microdrops.

| F3. Wettable powders | a) | b) | c) | d) |
|---|---|---|---|---|
| compound mixture | 5% | 25% | 50% | 80% |
| sodium ligninsulfonate | 4% | — | 3% | — |
| sodium laurylsulfate | 2% | 3% | — | 4% |
| sodium diisobutylnaphthalene sulfonate | — | 6% | 5% | 6% |
| octylphenol polyethoxylate (7–8 mol EO) | — | 1% | 2% | — |
| highly dispersed silica | 1% | 3% | 5% | 10% |
| kaolin | 88% | 62% | 35% | — |

The compound mixture is throughly mixed with the adjuvants and this mixture is ground in a suitable mill to give wettable powders which can be diluted with water to give suspensions of any desired concentration.

| F4. Coated granulates | a) | b) | c) |
|---|---|---|---|
| compound mixture | 0.1% | 5% | 15% |
| highly dispersed silica | 0.9% | 2% | 2% |
| inorganic carrier (Ø 0.1–1 mm) e.g. $CaCO_3$ or $SiO_2$ | 99.0% | 93% | 83% |

The compound mixture is dissolved in methylene chloride, the solution is sprayed on to the carrier, and the solvent is removed under vacuum.

| F5. Coated granulates | a) | b) | c) |
|---|---|---|---|
| compound mixture | 0.1% | 5% | 15% |
| polyethylene glycol 200 | 1.0% | 2% | 3% |
| highly dispersed silica | 0.9% | 1% | 2% |
| inorganic carrier (Ø 0.1–1 mm) e.g. $CaCO_3$ or $SiO_2$ | 98.0% | 92% | 80% |

The finely ground compound mixture is uniformly applied in a mixer to the kaolin moistened with polyethylene glycol. Non-dusty coated granulates are obtained in this manner.

| F6. Extruder granulates | a) | b) | c) | d) |
|---|---|---|---|---|
| compound mixture | 0.1% | 3% | 5% | 15% |
| sodium ligninsulfonate | 1.5% | 2% | 3% | 4% |
| carboxymethyl cellulose | 1.4% | 2% | 2% | 2% |
| kaolin | 97.0% | 93% | 90% | 79% |

The compound mixture is mixed with the adjuvants and the mixture is moistened with water. This mixture is extruded and then dried in a stream of air.

| F7. Dusts | a) | b) | c) |
|---|---|---|---|
| compound mixture | 0.1% | 1% | 5% |
| talcum | 39.9% | 49% | 35% |
| kaolin | 60.0% | 50% | 60% |

Ready for use dusts are obtained by mixing the the active ingredient with the carriers on a suitable mill.

| F8. Suspension concentrates | a) | b) | c) | d) |
|---|---|---|---|---|
| compound mixture | 3% | 10% | 25% | 50% |
| ethylene glycol | 5% | 5% | 5% | 5% |
| nonylphenol polyethoxylate (15 mol EO) | — | 1% | 2% | — |
| sodium ligninsulfonate | 3% | 3% | 4% | 5% |
| carboxymethyl cellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground compound mixture is intimately mixed with the adjuvants to give a suspension concentrate from which suspensions of any desired concentration can be prepared by dilution with water.

Example B1: Post-emergence phytotoxic action on maize of the herbicide of formula I and of the mixture of the herbicide with the safener of formula II Maize is sown in standard soil in plastic pots. Immediately after sowing, the test compounds are sprayed onto the plants in the form of an aqueous suspension (500 1 of water/ha) prepared from one of the formulations 1 to 10 described above. The concentration of herbicide of formula I is 8000 g/ha. The safener is applied in a concentration of 400 g/ha. The test plants are afterwards cultivated in a greenhouse under optimum conditions. After 22 days the phytotoxic action of the herbicide on the maize is evaluated (in percentage toxicity):

| Safener | Herbicide | Herbicide + Safener |
|---|---|---|
| 1.005 | 65 | 25 |
| 1.008 | 65 | 45 |
| 1.009 | 65 | 25 |
| 1.010 | 65 | 50 |
| 1.011 | 65 | 25 |
| 2.1 | 65 | 20 |
| 2.2 | 65 | 55 |

The results show that the damage caused to the cultivated plants by the herbicide can be markedly reduced with compounds of formula II.

What is claimed is:

1. A selective herbicidal composition comprising, in addition to customary inert formulation assistants, a mixture of a) a herbicidally effective mount of a compound of formula I

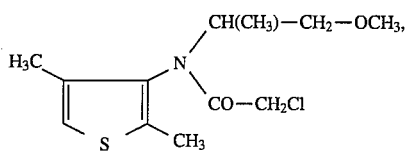 (I)

and b) to antagonise the herbicide, an antidotally effective amount of a compound of formula II R—CHYCl (II)

wherein R is a radical of formula

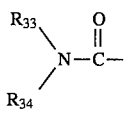

wherein $R_{33}$ and $R_{34}$ are each independently of the other $C_1$–$C_6$alkenyl; or $R_{33}$ and $R_{34}$, taken together, are

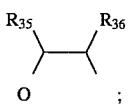

$R_{35}$ and $R_{36}$ are each independently of the other hydrogen or $C_1$–$C_6$alkyl;

or $R_{33}$ and $R_{34}$, taken together, are

$R_{37}$ and $R_{38}$ are each independently of the other $C_1$–$C_4$alkyl, or $R_{37}$ and $R_{38}$, taken together, are —$(CH_2)_5$—;

$R_{39}$ is hydrogen, $C_1$–$C_4$alkyl or

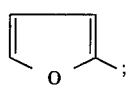

or $R_{33}$ and $R_{34}$, taken together, are

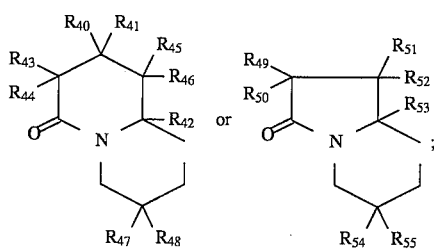

and $R_{40}$, $R_{41}$, $R_{42}$, $R_{43}$, $R_{44}$, $R_{45}$, $R_{46}$, $R_{47}$, $R_{48}$, $R_{49}$, $R_{50}$, $R_{51}$, $R_{52}$, $R_{53}$, $R_{54}$ and $R_{55}$ are each independently of one another hydrogen or $C_1$–$C_4$alkyl, or R is a radical of formula

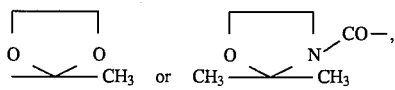

or R is a radial formula

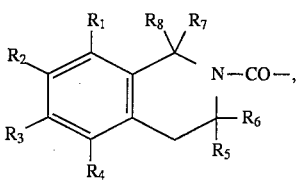

wherein $R_1$, $R_2$, $R_3$ and $R_4$ are each independently of one another hydrogen, $C_1$–$C_4$alkyl, $C_1$–$C_4$alkoxy or $C_1$–$C_4$haloalkyl, $R_5$, $R_6$, $R_7$ and $R_8$ are each independently of one another hydrogen, $C_1$–$C_4$alkyl or $C_1$–$C_4$haloalkyl, or R is a radical of formula

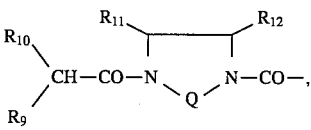

wherein $R_9$ is $C_1$–$C_4$alkyl or halogen, $R_{10}$ is halogen, $R_{11}$ and $R_{12}$ are each independently of the other hydrogen or $C_1$–$C_4$alkyl, and Q is $C_1$–$C_4$alkylene or alkyl-substituted $C_1$–$C_4$alkylene, or R is a radical of formula

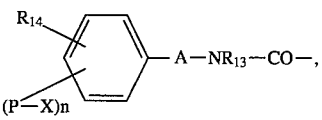

wherein $R_{14}$ is hydrogen, halogen, $C_1$–$C_4$alkyl, dioxymethylene, $C_1$–$C_4$alkoxy, $C_1$–$C_4$alkenyloxy, $C_2$–$C_4$alkynyloxy or cyano-$C_1$–$C_4$alkyl, P is $C_1$–$C_4$alkyl, $C_2$–$C_4$ alkenyl, $C_2$–$C_4$alkynyl, $C_3$–$C_8$cycloalkyl, $C_1$–$C_4$alkoxy-$C_1$–$C_4$alkyl, $C_2$–$C_4$ alkeneoxy-$C_1$–$C_4$alkyl, $C_2$–$C_4$alkyneoxy-$C_1$–$C_4$alkyl, $C_1$–$C_4$alkylthio-$C_1$–$C_4$ alkyl, $C_2$–$C_4$alkenylthio-$C_1$–$C_4$alkyl, $C_2$–$C_4$alkynylthio-$C_1$–$C_4$alkyl, $C_1$–$C_4$alkylsulfinyl-$C_1$–$C_4$alkyl, $C_1$–$C_4$alkylsulfonyl-$C_1$–$C_4$alkyl, halo-$C_1$–$C_4$alkyl, cyano-$C_1$–$C_4$alkyl, 2,2-di-$C_1$–$C_4$alkoxy-$C_1$–$C_4$alkyl, 1,3-dioxolan-2-yl-$C_1$–$C_4$alkyl, 1,3-dioxolan-4-yl-$C_1$–$C_4$alkyl, 2,2-di-$C_1$–$C_4$alkyl-1,3-dioxolan-4 -yl-$C_1$–$C_4$alkyl, 1,3-dioxan-2-yl-$C_1$–$C_4$alkyl, 2-benzopyranyl-$C_1$–$C_4$alkyl, $C_1$–$C_4$ alkoxycarbonyl or $C_2$–$C_4$alkenyloxycarbonyl or tetrahydrofurfuryl-$C_1$–$C_4$alkyl, the group P-X may also be halogen-$C_1$–$C_4$alkyl, X is O, S, SO or $SO_2$, n is 1, 2 or 3, A is a $C_1$–$C_8$hydrocarbon radical or $C_1$–$C_8$hydrocarbon radical which is substituted by alkoxy, alkylthio, fluoro, cyano or haloalkyl, and $R_{13}$ is hydrogen, a $C_1$–$C_5$hydrocarbon radical, a $C_1$–$C_5$hydrocarbon radical which is substituted by alkoxy, polyalkoxy, halogen, cyano or trifluoromethyl, $C_3$–$C_8$cycloalkyl, $C_1$–$C_4$alkyl-$C_3$–$C_8$cycloalkyl, di-$C_1$–$C_4$alkoxy-$C_1$ –$C_4$alkyl, 1,3-dioxolan-2-yl-$C_1$–$C_4$alkyl, 1,3-dioxolan-4-yl-$C_1$–$C_4$alkyl, 1,3 -dioxan-2-yl-$C_1$–$C_4$alkyl, furyl-$C_1$–$C_4$alkyl, tetrahydrofuryl-$C_1$-$C_4$alkyl or a radical of formula —$NHCO_2R_{01}$, —$CH_2CO_2R_{01}$, —$CH(CH_3)CO_2R_{01}$ or —$CH(R_{02})$—$C(R_{03})$=$NOR_{04}$, wherein $R_{01}$ is methyl, ethyl, propyl, isopropyl or allyl, $R_{02}$ and $R_{03}$ are each hydrogen or $C_1$-$C_4$alkyl, and $R_{04}$ is hydrogen, $C_1$-$C_4$alkyl, $C_2$-$C_4$alkenyl or $C_2$-$C_4$alkynyl, or R is a radical of formula $(H_5C_2O)_2P(O)CH_2NHCO$—

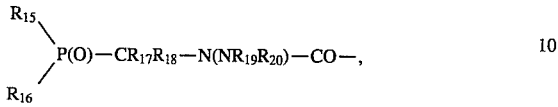

wherein $R_{15}$ and $R_{16}$ are each independently of the other hydroxyl, $C_1$-$C_4$alkyl, aryl, $C_1$-$C_4$alkoxy, $C_2$-$C_4$alkenyloxy, $C_2$-$C_4$alkynyloxy, $C_2$-$C_4$haloalkoxy, $C_2$-$C_8$alkoxyalkoxy, $C_1$-$C_4$cyanoalkoxy, $C_1$-$C_4$ phenylalkoxy or aryloxy, or aryloxy which is substituted by halogen, cyano, nitro or $C_1$-$C_4$alkoxy, $R_{17}$ is hydrogen, $C_1$-$C_4$alkyl or phenyl, or phenyl which is substituted by halogen, cyano, nitro or $C_1$-$C_4$alkoxy, $R_{18}$ is hydrogen, or $C_1$-$C_4$alkyl, $R_{19}$ is hydrogen or a radical of formula —$COCX_1X_2$—$R_{06}$ or a halogen-substituted alkenoyl radical containing 2 to 4 carbon atoms in the alkenyl moiety, wherein $X_1$ and $X_2$ are each independently of the other halogen, or a radical of formula —$COOR_{07}$ or —$COR_{08}$ or a $C_1$-$C_4$alkyl, $C_2$-$C_4$alkenyl or $C_1$-$C_4$phenylalkyl radical which can be substituted at the phenyl ring by halogen, cyano, nitro or $C_1$-$C_4$alkoxy, and $R_{20}$ is hydrogen, $C_1$-$C_4$alkyl, $C_2$-$C_4$ alkenyl or $C_2$-$C_4$alkynyl, $R_{06}$ is hydrogen, halogen or $C_1$-$C_6$alkyl, $R_{07}$ is $C_1$-$C_4$alkyl, $C_1$-$C_4$phenylalkyl or $C_1$-$C_4$phenylalkyl which is substituted in the phenyl nucleus by halogen, cyano, nitro or $C_1$-$C_4$alkoxy, and $R_{08}$ is $C_1$-$C_4$alkyl, $C_2$-$C_4$alkenyl, $C_2$-$C_4$ alkynyl, phenyl, $C_1$-$C_4$phenylalkyl or $C_1$-$C_4$phenylalkyl which is substituted in the phenyl nucleus by halogen, cyano, nitro or $C_1$-$C_4$alkoxy, or R is a radical of formula

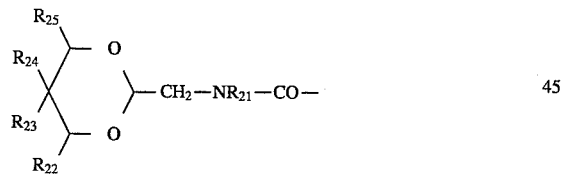

or of formula

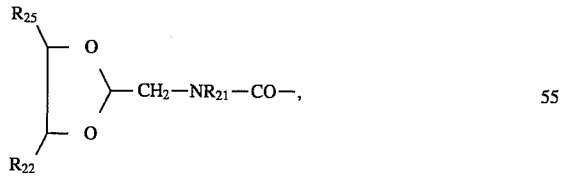

wherein $R_{21}$ is methyl, ethyl, propyl, 1-methylethyl, 2-propenyl, 2-butenyl, 1,1-dimethyl-2-propenyl, 2-propynyl or 2-methyl-2-propynyl, and $R_{22}$, $R_{23}$, $R_{24}$ and $R_{25}$ are each independently of one another hydrogen or methyl, and Y is chloro, or Y is hydrogen if R is a radical of formula $(H_5C_2O)_2P(O)CH_2NHCO$—.

2. A composition according to claim 1, wherein R is a radical of formula

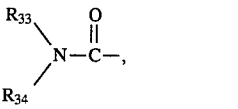

wherein $R_{33}$ and $R_{34}$ together are

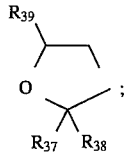

$R_{37}$ and $R_{38}$ are each independently of the other $C_1$-$C_4$alkyl; or $R_{37}$ and $R_{38}$ together are —$(CH_2)_5$—; and $R_{39}$ is hydrogen, $C_1$-$C_4$alkyl or

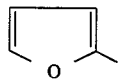

3. A composition according to claim 1, wherein R is a radical of formula

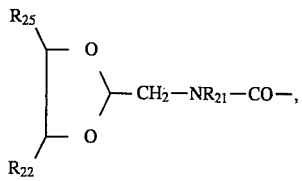

wherein $R_{21}$ is methyl, ethyl, propyl, 2-propenyl or 2-butenyl, $R_{22}$ and $R_{25}$ are hydrogen.

4. A composition according to claim 3, wherein $R_{21}$ is 2-propenyl.

5. A composition according to claim 1, wherein R is a radical of formula

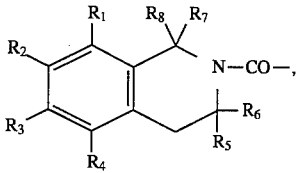

wherein $R_1$ to $R_8$ are each independently of one another hydrogen or $C_1$-$C_4$alkyl.

6. A composition according to claim 5, wherein $R_1$ to $R_7$ are hydrogen and $R_8$ is methyl.

7. A composition according to claim 1, wherein R is a radical of formula

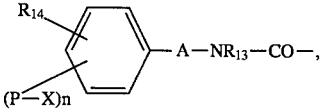

wherein $R_{14}$ is hydrogen, $C_1$-$C_4$alkyl or $C_1$-$C_4$alkoxy, P is $C_1$-$C_4$alkyl, $C_2$-$C_4$alkenyl or $C_2$-$C_4$ alkynyl, X is O or S, n is 1, A is a $C_1$-$C_8$hydrocarbon radical and $R_{13}$ is hydrogen or a $C_1$-$C_5$hydrocarbon radical.

8. A composition according to claim 7, wherein $R_{14}$ is $C_1$-$C_4$alkoxy, P is $C_1$-$C_4$alkyl, X is O, A is $C_1$-$C_4$alkylene and $R_{13}$ is $C_1$-$C_4$alkyl.

9. A composition according to claim 8, wherein $R_{14}$ is methoxy, P is methyl, A is methylene and $R_{13}$ is isopropyl.

10. A composition according to claim 1, wherein R is a radical of formula

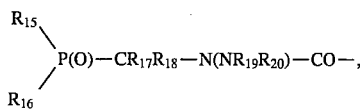

wherein $R_{15}$ and $R_{16}$ are each independently of the other hydroxyl, $C_1$-$C_4$alkyl or $C_1$-$C_4$alkoxy, $R_{17}$ and $R_{18}$ are each independently of the other hydrogen or $C_1$-$C_4$alkyl, and $R_{19}$ is hydrogen or a radical of formula —$COOR_{07}$, wherein $R_{07}$ is $C_1$-$C_4$alkyl, and $R_{20}$ is hydrogen or $C_1$-$C_4$alkyl.

11. A composition according to claim 10, wherein $R_{16}$ and $R_{15}$ are $C_1$-$C_4$alkoxy, $R_{17}$ and $R_{18}$ are hydrogen, $R_{19}$ is a radical of formula —$COOR_{07}$, wherein $R_{07}$ is $C_1$-$C_4$alkyl, and $R_{20}$ is hydrogen.

12. A composition according to claim 11, wherein $R_{15}$ and $R_{16}$ are isopropoxy and $R_{19}$ is —$COOC_2H_5$.

13. A composition according to claim 1, wherein the compound of formula II is selected from the group consisting of a compound of formula III

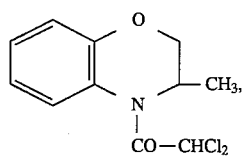 (III)

a compound of formula IV

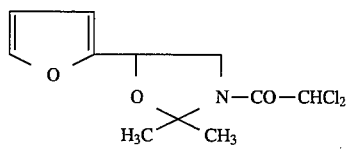 (IV)

and a compound of formula V

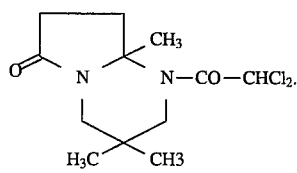 (V)

14. A method of selectively controlling weeds and grasses in crops of cultivated plants, which comprises treating said plants, the seeds or the locus thereof, concurrently or separately, with an effective amount of a herbicide of formula I

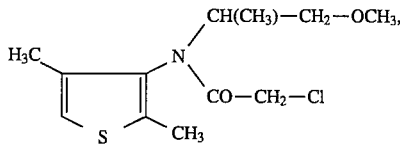 (I)

and, to antagonise said herbicide, an antidotally effective amount of a compound of formula II R—CHYCl (II)

wherein R is a radical of formula

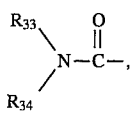

$R_{33}$ and $R_{34}$, are each independently of the other $C_1$-$C_6$alkyl or $C_2$-$C_6$ alkenyl; or $R_{33}$ and $R_{34}$, taken together, are

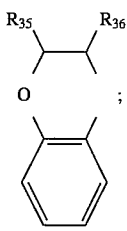

$R_{35}$ and $R_{36}$ are each independently of the other hydrogen or $C_1$-$C_6$alkyl; or $R_{33}$ and $R_{34}$, taken together, are

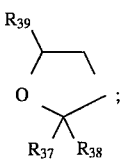

$R_{37}$ and $R_{38}$ are each independently of the other $C_1$-$C_4$alkyl, or $R_{37}$ and $R_{38}$, taken together, are —$(CH_2)_5$-;

$R_{39}$ is hydrogen, $C_1$-$C_4$alkyl or

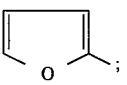

or $R_{33}$ and $R_{34}$, taken together, are

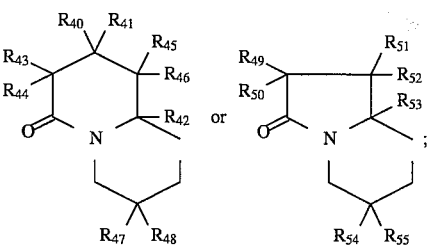

and $R_{40}$, $R_{41}$, $R_{42}$, $R_{43}$, $R_{44}$, $R_{45}$, $R_{46}$, $R_{47}$, $R_{48}$, $R_{49}$, $R_{50}$, $R_{51}$, $R_{52}$, $R_{53}$, $R_{54}$ and $R_{55}$ are each independently of one another hydrogen or $C_1$-$C_4$alkyl, or R is a radical of formula

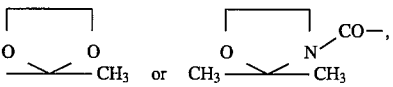

or R is a radical of formula

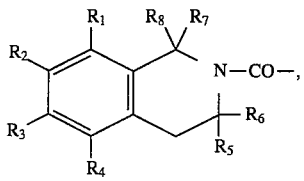

wherein $R_1$, $R_2$, $R_3$ and $R_4$ are each independently of one another hydrogen, $C_1$–$C_4$alkyl, $C_1$–$C_4$alkoxy or $C_1$–$C_4$haloalkyl, $R_5$, $R_6$, $R_7$ and $R_8$ are each independently of one another hydrogen, $C_1$–$C_4$alkyl or $C_1$–$C_4$haloalkyl, or R is a radical of formula

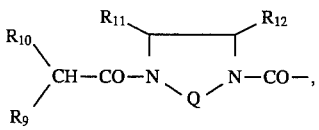

wherein $R_9$ is $C_1$–$C_4$alkyl or halogen, $R_{10}$ is halogen, $R_{11}$ and $R_{12}$ are each independently of the other hydrogen or $C_1$–$C_4$alkyl, and Q is $C_1$–$C_4$alkylene or alkyl-substituted $C_1$–$C_4$alkylene, or R is a radical of formula

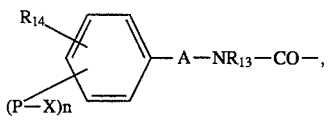

wherein $R_{14}$ is hydrogen, halogen, $C_1$–$C_4$alkyl, dioxymethylene, $C_1$–$C_4$alkoxy, $C_2$–$C_4$alkenyloxy, $C_2$–$C_4$ alkynyloxy or cyano-$C_1$–$C_4$alkyl, P is $C_1$–$C_4$alkyl, $C_2$–$C_4$alkenyl, $C_2$–$C_4$alkynyl, $C_3$–$C_8$ cycloalkyl, $C_1$–$C_4$alkoxy-$C_1$–$C_4$alkyl, $C_2$–$C_4$alkenoxy-$C_1$–$C_4$alkyl, $C_2$–$C_4$alkynoxy-$C_1$–$C_4$alkyl, $C_1$–$C_4$ alkylthio-$C_1$–$C_4$alkyl, $C_2$–$C_4$alkenylthio-$C_1$–$C_4$alkyl, $C_2$–$C_4$alkynylthio-$C_1$–$C_4$alkyl, $C_1$–$C_4$alkylsulfinyl-$C_1$–$C_4$ alkyl, $C_1$–$C_4$alkylsulfonyl-$C_1$–$C_4$alkyl, halo-$C_1$–$C_4$alkyl, cyano-$C_1$–$C_4$alkyl, 2,2-di-$C_1$–$C_4$ alkoxy-$C_1$–$C_4$alkyl, 1,3-dioxolan-2-yl-$C_1$–$C_4$alkyl, 1,3-dioxolan-4-yl-$C_1$–$C_4$alkyl, 2,2-di-$C_1$–$C_4$alkyl-1,3-dioxolan-4 -yl-$C_1$–$C_4$alkyl, 1,3-dioxan-2-yl-$C_1$–$C_4$alkyl, 2-benzopyranyl-$C_1$–$C_4$alkyl, $C_1$–$C_4$ alkoxycarbonyl or $C_2$–$C_4$alkenyloxycarbonyl or tetrahydrofurfuryl-$C_1$–$C_4$alkyl, the group P-X is also halo-$C_1$–$C_4$ alkyl, X is O, S, SO or $SO_2$, n is 1, 2 or 3, A is a $C_1$–$C_8$hydrocarbon radical or a $C_1$–$C_8$ hydrocarbon radical which is substituted by alkoxy, alkylthio, fluoro, cyano or haloalkyl, and $R_{13}$ is hydrogen, a $C_1$–$C_5$hydrocarbon radical, a $C_1$–$C_5$hydrocarbon radical which is substituted by alkoxy, polyalkoxy, halogen, cyano or trifluoromethyl; $C_3$–$C_8$cycloalkyl, $C_1$–$C_4$alkyl-$C_3$–$C_8$cycloalkyl, di-$C_1$–$C_4$alkoxy-$C_1$–$C_4$alkyl, 1,3-dioxolan-2-yl-$C_1$–$C_4$alkyl, 1,3 -dioxolan-4-yl-$C_1$–$C_4$alkyl 1,3-dioxan-2-yl-$C_1$–$C_4$alkyl, furyl-$C_1$–$C_4$alkyl, tetrahydrofuryl-$C_1$–$C_4$ alkyl, or a radical of formula —$NHCO_2R_{01}$, —$CH_2CO_2R_{01}$, —$CH(CH_3)CO_2R_{01}$ or —$CH(R_{02})$—$C(R_{03})$=$NOR_{04}$, wherein $R_{01}$ is methyl, ethyl, propyl, isopropyl or allyl, $R_{02}$ and $R_{03}$ are each hydrogen or $C_1$–$C_4$alkyl, and $R_{04}$ is hydrogen, $C_1$–$C_4$alkyl, $C_2$–$C_4$alkenyl or $C_2$–$C_4$alkynyl, or R is a radical of formula $(H_5C_2O)_2P(O)CH_2NHCO$— or

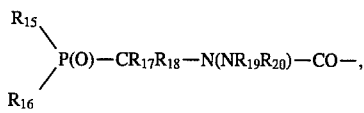

wherein $R_{15}$ and $R_{16}$ are each independently of the other hydroxyl, $C_1$–$C_4$alkyl, aryl, $C_1$–$C_4$ alkoxy, $C_2$–$C_4$alkenyloxy, $C_2$–$C_4$alkynyloxy, $C_2$–$C_4$haloalkoxy, $C_2$–$C_8$ alkoxyalkoxy, $C_1$–$C_4$cyanoalkoxy, $C_1$–$C_4$phenylalkoxy or aryloxy or aryloxy which is substituted by halogen, cyano, nitro or $C_1$–$C_4$alkoxy, $R_{17}$ is hydrogen, $C_1$–$C_4$alkyl or phenyl, or phenyl which is substituted by halogen, cyano, nitro or $C_1$–$C_4$alkoxy, $R_{18}$ is hydrogen, or $C_1$–$C_4$alkyl, $R_{19}$ is hydrogen or a radical of formula —$COCX_1X_2$-$R_{06}$, or an alkenoyl radical which contains 2 to 4 carbon atoms in the alkenyl moiety and which is substituted by halogen, and $X_1$ and $X_2$ are each independently of the other hydrogen or halogen, or is a radical of formula —$COOR_{07}$ or —$COR_{08}$ or a $C_1$–$C_4$alkyl, $C_2$–$C_4$alkenyl or $C_1$–$C_4$phenylalkyl radical which can be substituted at the phenyl ring by halogen, cyano, nitro or $C_1$–$C_4$alkoxy, and $R_{20}$ is hydrogen, $C_1$–$C_4$alkyl, $C_2$–$C_4$alkenyl or $C_2$–$C_4$ alkynyl, $R_{06}$ is hydrogen, halogen or $C_1$–$C_6$alkyl, $R_{07}$ is $C_1$–$C_4$alkyl, $C_1$–$C_4$ phenylalkyl or $C_1$–$C_4$phenylalkyl which is substituted in the phenyl moiety by halogen, cyano, nitro or $C_1$–$C_4$alkoxy, and $R_{08}$ is $C_1$–$C_4$alkyl, $C_2$–$C_4$alkenyl, $C_2$–$C_4$alkynyl, phenyl, $C_1$–$C_4$phenylalkyl or $C_1$–$C_4$ phenylalkyl which is substituted in the phenyl moiety by halogen, cyano, nitro or $C_1$–$C_4$alkoxy, or R is a radical of formula

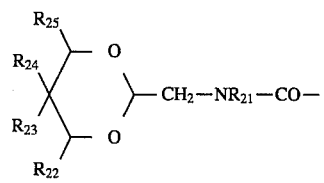

or of the formula

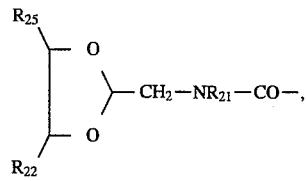

wherein $R_{21}$ is methyl, ethyl, propyl, 1-methylethyl, 2-propenyl, 2-butenyl, 1,1-dimethyl-2-propenyl, 2-propynyl or 2-methyl-2 -propynyl, and $R_{22}$, $R_{23}$, $R_{24}$ and $R_{25}$ are each independently of one another hydrogen or methyl, and Y is chloro, or Y is hydrogen if R is a radical of formula $(H_5C_2O)_2P(O)CH_2NHCO$—.

15. A method according to claim 14, wherein the plants, the seeds or the locus thereof is treated with 0.001 to 5 kg/ha of a compound of formula I and 0.005 to 0.5 kg/ha of a compound of formula II.

16. A method according to claim 14, wherein the cultivated plants are maize.

* * * * *